United States Patent
Horn et al.

(10) Patent No.: US 10,106,835 B2
(45) Date of Patent: Oct. 23, 2018

(54) METHODS OF PRODUCING STERILIZED DIAGNOSTIC TEST ELEMENTS

(71) Applicant: Roche Diabetes Care, Inc., Indianapolis, IN (US)

(72) Inventors: Carina Horn, Biblis (DE); Nelli Steinke, Lampertheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 273 days.

(21) Appl. No.: 15/218,171

(22) Filed: Jul. 25, 2016

(65) Prior Publication Data

US 2016/0333391 A1 Nov. 17, 2016

Related U.S. Application Data

(60) Division of application No. 13/493,251, filed on Jun. 11, 2012, now Pat. No. 9,399,792, which is a continuation of application No. PCT/EP2010/069368, filed on Dec. 10, 2010.

(30) Foreign Application Priority Data

Dec. 11, 2009 (EP) .................................... 09178958

(51) Int. Cl.
*C12Q 1/32* (2006.01)
*C12Q 1/54* (2006.01)
*A61L 2/08* (2006.01)
*A61L 2/28* (2006.01)

(52) U.S. Cl.
CPC ................ *C12Q 1/54* (2013.01); *A61L 2/081* (2013.01); *A61L 2/087* (2013.01); *A61L 2/28* (2013.01); *C12Y 101/01047* (2013.01); *A61L 2202/11* (2013.01); *G01N 2333/904* (2013.01)

(58) Field of Classification Search
None
See application file for complete search history.

(56) References Cited

U.S. PATENT DOCUMENTS

| | | | |
|---|---|---|---|
| 5,196,340 A | 3/1993 | Miyamoto | |
| 5,801,006 A | 9/1998 | Kaufman | |
| 5,879,297 A | 3/1999 | Haynor et al. | |
| 6,740,215 B1 | 5/2004 | Nakaminami et al. | 204/403.14 |
| 7,341,846 B2 | 3/2008 | Yamaoka et al. | |
| 7,553,615 B2 | 6/2009 | Heindl et al. | 435/4 |
| 2008/0213808 A1 | 9/2008 | Knappe | |
| 2009/0010802 A1 | 1/2009 | Joseph et al. | |
| 2010/0292609 A1 | 11/2010 | Zimmer et al. | |

FOREIGN PATENT DOCUMENTS

| | | |
|---|---|---|
| CN | 1250161 A | 4/2000 |
| EP | 0 951 939 A2 | 10/1999 |
| EP | 1 167 519 A1 | 1/2002 |
| EP | 1 293 574 B1 | 3/2003 |
| EP | 1 430 831 A1 | 6/2004 |
| EP | 1 964 927 A1 | 9/2008 |
| EP | 1 992 284 A1 | 11/2008 |
| JP | 2004117233 A | 4/2004 |
| WO | WO 98/33936 A1 | 8/1998 |
| WO | WO 01/49247 A2 | 7/2001 |
| WO | WO 03/106702 A1 | 12/2003 |
| WO | WO 2005/084530 A2 | 9/2005 |
| WO | WO/2005/104948 A1 | 11/2005 |
| WO | WO 2007/012494 A1 | 2/2007 |
| WO | WO 2009/126942 A2 | 10/2009 |
| WO | WO 2011/070149 A1 | 6/2011 |

OTHER PUBLICATIONS

James T. Slama et al., Carbanicotinamide Adenine Dinucleotide: Synthesis and Enzymological Properties of a Carbocyclic Analogue of Oxidized Nicotinamide Adenine Dinucleotide, Biochemistry, 1988, pp. 183-193, vol. 27 No. 1, Copyright 1988 American Chemical Society.

James T. Slama et al., Inhibition of NAD Glycohydrolase and ADP-ribosyl Transferases by Carbocyclic Analogues of Oxidized Nicotinamide Adenine Dinucleotide, Biochemistry, 1989, pp. 7688-7694, XP-002502968, vol. 28 No. 19, Copyright 1989 American Chemical Society.

Edward J. Hutchinson et al., Synthesis of Carbocyclic Nad+ Containing a Methyleneblsphophonate Linkage for the Investigation of ADP-Ribosyl Cyclase, Chem. Commun., 1996, pp. 2765-2766, Issue 24.

Canadian Office Action, dated Jan. 17, 2014, Patent Application No. 2,782,031, 4 pages.

Bisse and Vonderschmitt, "Immobilization of glucose dehydrogenase by titanium tetrachloride", FEBS Letters 93(1): 102-104 (Sep. 1978).

Deng et al.,"A sensitive NADH and glucose biosensor tuned by visible light based on thionine bridged carbon nanotubes and gold (Continued)

*Primary Examiner* — Anand U Desai

(57) ABSTRACT

In one non-limiting aspect, sterilizable reagent materials for diagnostic elements are provided. In other aspects, sterilized elements and techniques for producing the same are disclosed. In one embodiment, a sterilized element includes a chemical detection reagent including at least one component that is sensitive to ionizing radiation. The sterilized element is also mediator-free and the at least one component sensitive to ionizing radiation is present in a functional form in a proportion of ≥80% based on the total amount of the respective component in the diagnostic element before sterilization. In certain aspects, the at least one component sensitive to ionizing radiation includes one or both of an enzyme and a coenzyme. Other aspects include, but are not limited to, unique methods, techniques, products, systems and devices involving sterilizable reagent materials or sterilized elements.

16 Claims, 4 Drawing Sheets

(56) References Cited

OTHER PUBLICATIONS nanoparticles multilayer", Biosensors and Bioelectronics 24: 951-957 (2008).

METHODS OF PRODUCING STERILIZED DIAGNOSTIC TEST ELEMENTS

CROSS-REFERENCE TO RELATED APPLICATIONS

This patent application is a divisional of U.S. patent application Ser. No. 13/493,251 (filed 11 Jun. 2012; now U.S. Pat. No. 9,399,792, issued 26 Jul. 2016) which is a continuation of Int'l Patent Application No. PCT/EP2010/069368 (filed 10 Dec. 2010), which claims priority to and the benefit of EP Patent Application No. 09178958.6 (filed 11 Dec. 2009). Each patent application is incorporated herein by reference as if set forth in its entirety.

FIELD OF THE INVENTION

The present application concerns a diagnostic test element as well as a process for its production.

BACKGROUND

Diagnostic elements are important components of clinically relevant analytical methods. This primarily concerns the measurement of analytes such as metabolites or substrates which are determined directly or indirectly, for example, with the aid of a specific enzyme for the analyte. The analytes are converted with the aid of an enzyme-coenzyme complex and subsequently quantified. In this process, the analyte to be determined is contacted with a suitable enzyme, a coenzyme and optionally a mediator and the coenzyme is physic-chemically changed by the enzymatic reaction. For example, the coenzyme may be oxidized or reduced by the enzymatic reaction.

If a mediator is used, it typically transfers the electrons released from the reduced coenzyme during the conversion of the analyte onto an optical indicator or the conductive components of an electrode so that the process can be detected photometrically or electrochemically. A calibration yields a direct relationship between the measured value and the concentration of the analyte to be determined.

The sterilizability of such test elements is of major importance, particularly when they are used for diagnostic purposes. Diagnostic test elements which are known from the prior art and used to determine blood glucose for example have the disadvantage that they have a low stability with regard to ionizing radiation or other physical or chemical agents that are conventionally used for sterilization. Similarly, certain features of these test elements, such as the enzyme system, may exhibit significant damage after sterilization. For example, certain test elements that are currently commercially available such as, by way of non-limiting example, the Accu-Check Active®, Accu-check Aviva® or the biosensors described in EP Patent Application Publication No. EP 1 430 831, which contain a pyrroloquinoline quinone (PQQ)-dependent enzyme and a mediator for electron transfer, show a significant loss of enzyme activity after sterilization with ionizing radiation.

A known measure that is used to compensate for damage to the enzyme system of biochemical test elements caused by sterilization is to overdose the enzyme system. EP Patent Publication No. EP I 293 574 BI discloses electrochemical sensors which comprise a PQQ-dependent glucose dehydrogenase in combination with a phenothiazine mediator where the PQQ-dependent glucose dehydrogenase is used at a concentration of 20 enzyme units. After sterilization using electron radiation at a dose of 25 kilogray (kGy), sensors are obtained which, depending on the formulation of the enzyme system, have a high absolute amount of functional enzyme due to the overdosing of the enzyme system despite losses due to sterilization.

However, overdosing of the enzyme system in biochemical test elements has various disadvantages. For example, in addition to overdosing of the enzyme system being uneconomical and resulting in significantly higher production costs when producing consumables on a large industrial scale, high concentrations of enzymes in particular can cause problems in relation to solubility and/or viscosity which make it difficult to apply the enzyme to a suitable carrier.

One non-limiting object of the present application is to provide a stable biochemical test element for determining analytes such as glucose and that at least partially eliminates the disadvantages of the prior art. More particularly but not exclusively, in one aspect a test element that has a high proportion of active enzyme or active coenzyme and ensures good performance after sterilization and without overdosing the enzyme system is desired.

BRIEF SUMMARY

In one non-limiting aspect, sterilizable reagent materials for diagnostic elements are provided. In other aspects, sterilized diagnostic elements and techniques for the production of the same are disclosed. Other aspects include, but are not limited to, unique methods, techniques, products, systems and devices involving sterilizable reagent materials or sterilized diagnostic elements.

In one embodiment, a sterilized diagnostic element includes a chemical detection reagent including at least one component that is sensitive to ionizing radiation. The sterilized diagnostic element is also mediator-free and the at least one component sensitive to ionizing radiation is present in a functional form in a proportion of $\geq 80\%$ based on the total amount of the respective component in the diagnostic element before sterilization. In certain aspects, the at least one component sensitive to ionizing radiation includes one or both of an enzyme and a coenzyme.

In another embodiment, a storage container includes a diagnostic element and a sample collection element. The sterilized diagnostic element includes a chemical detection reagent including at least one component that is sensitive to ionizing radiation. The sterilized diagnostic element is also mediator-free and the at least one component sensitive to ionizing radiation is present in a functional form in a proportion of $\geq 80\%$ based on the total amount of the respective component in the diagnostic element before sterilization. In certain aspects, the at least one component sensitive to ionizing radiation includes one or both of an enzyme and a coenzyme.

In yet another embodiment, a method for producing a sterilized diagnostic element includes providing a mediator-free diagnostic element including a chemical detection reagent. The chemical detection reagent includes at least one component sensitive to ionizing radiation, and the at least one component sensitive to ionizing radiation includes one or both of an enzyme and a coenzyme. The method also includes sterilizing the mediator-free diagnostic element with ionizing radiation, and the ionizing radiation includes one or both of electron radiation and gamma radiation.

Other aspects include unique compositions, methods, techniques, systems and devices involving diagnostic element sterilization.

Further embodiments, forms, objects, features, advantages, aspects, and benefits shall become apparent from the following description and drawings.

DETAILED DESCRIPTION

Figure 1:
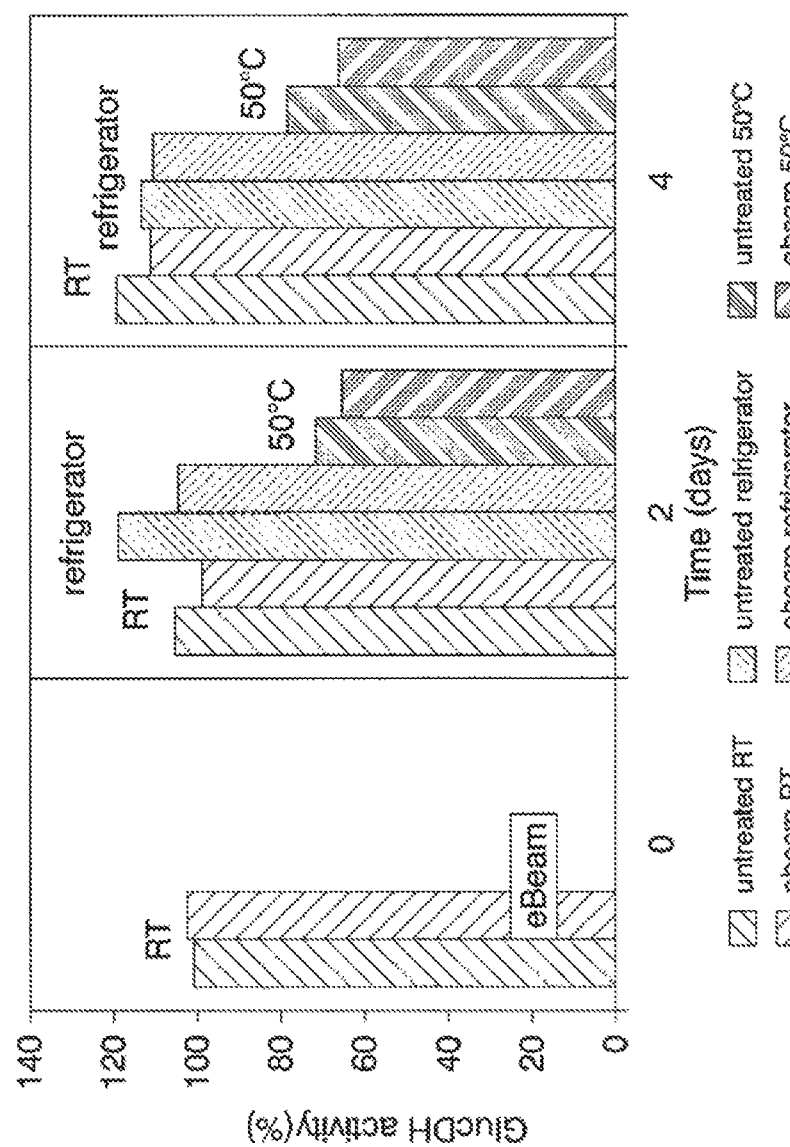
FIG. 1 is a graphical illustration of activity of glucose dehydrogenase (GlucOH) in a diagnostic element that includes glucose dehydrogenase and nicotinamide adenine dinucleotide before and after sterilization with electron radiation (eBeam; dose 25 kGy). The determination of glucose dehydrogenase activity took place immediately after production (0 days) as well as 2 and 4 days after storage of the diagnostic element at 5° C. (refrigerator), room temperature (RT) or 50° C.

In one non-limiting aspect, sterilizable reagent materials for diagnostic elements are provided. In other aspects, sterilized diagnostic elements and techniques for the production of the same are disclosed. Other aspects include, but are not limited to, unique methods, techniques, products, systems and devices involving sterilizable reagent materials or sterilized diagnostic elements.

In one embodiment, a diagnostic element includes a chemical detection reagent which has at least one component that is sensitive to ionizing radiation. The diagnostic element has been subjected to a sterilization and the at least one component that is sensitive to ionizing radiation is present in a functional form in a proportion of ≥80% based on the total amount of the at least one component in the diagnostic element before sterilization.

Diagnostic elements, such as test tapes or test strips for example, which include a chemical detection reagent containing at least one component that is sensitive to ionizing radiation and exhibit no or only slight damage to the at least one component after sterilization have been surprisingly discovered.

In one form, the chemical detection reagent used in the diagnostic elements disclosed herein can include any components that are suitable for determining an analyte using, by way of non-limiting example, optical or electrochemical means. Non-limiting examples of these components include polypeptides, coenzymes, optical indicators, mediators and auxiliary substances and/or additives. It should be understood that the chemical detection reagent can be provided in any form. In one particular form, the chemical detection reagent is a component of at least one reagent layer that is applied to a suitable carrier and, where appropriate, can be used at the same time to detect the analyte.

The at least one component that is sensitive to ionizing radiation can be any component of the chemical detection reagent that is required for the diagnostics of an analyte to be determined; i.e., one that is directly or indirectly involved in the physico-chemical conversion of the analyte. As used herein, the term "sensitive to ionizing radiation" means that the at least one component can be physico-chemically changed and/or its function can be impaired by ionizing radiation under the respective environmental conditions; i.e., at the pressure, temperature and relative air humidity that prevail in each case.

In view of the foregoing, it should be appreciated that it is possible after sterilization of the diagnostic element for the at least one component that is sensitive to ionizing radiation to be present in a functional form in a proportion of 100% based on the total amount of the at least one component in the diagnostic element before sterilization where the above-mentioned stability criteria in each case apply to the total diagnostic element.

In one or more forms, the at least component that is sensitive to ionizing radiation is a polypeptide, a coenzyme, an optical indicator or a combination thereof. In one particular but non-limiting form, the at least component that is sensitive to ionizing radiation is or includes a polypeptide. Non-limiting examples of such include any polypeptide which meets the respective requirements and is considered to be suitable by a person skilled in the art. In one form, the polypeptide is an enzyme, such as a coenzyme-dependent enzyme. Examples of these enzymes include, amongst others, dehydrogenases, oxidases such as glucose oxidase (EC 1.1.3.4) or cholesterol oxidase (EC 1.1.3.6) for example, aminotransferases such as aspartate or alanine aminotransferase for example, 5'-nucleotidase, creatine kinase and diaphorase (EC 1.6.99.2).

In one more specific embodiment, a nicotinamide adenine dinucleotide (NAD/NADH)-dependent dehydrogenase or a nicotinamide adenine dinucleotide phosphate (NADP/NADPH)-dependent dehydrogenase is used as the enzyme. In more particular forms of this embodiment, the enzyme is selected in from the group of an alcohol dehydrogenase (EC 1.1.1.1; EC 1.1.1.2), an L-amino acid dehydrogenase (EC 1.4.1.5), a glucose dehydrogenase (EC 1.1.1.47), a glucose-6-phosphate dehydrogenase (EC 1.1.1.49), a glycerol dehydrogenase (EC 1.1.1.6), a 3-hydroxybutyrate dehydrogenase (EC 1.1.1.30), a lactate dehydrogenase (EC 1.1.1.27; 1.1.1.28), a malate dehydrogenase (EC 1.1.1.37) and a sorbitol dehydrogenase. In another more particular form, the enzyme is a glucose dehydrogenase (EC 1.1.1.47) or a glucose-6-phosphate dehydrogenase (EC 1.1.1.49).

Additionally or alternatively, the at least one component that is sensitive to ionizing radiation may also be or include a coenzyme. It is contemplated that the use of any coenzyme is possible, although a NAD(P)/NAD(P)H compound is used as the coenzyme in one particular but non-limiting form. The term NAD(P)/NAD(P)H compound as used herein encompasses naturally occurring NAD(P)/NAD(P)H compounds, such as nicotinamide adenine dinucleotide (NAD/NADH) and nicotinamide adenine dinucleotide phosphate (NADP/NADPH) for example, as well as artificial NAD(P)/NAD(P)H compounds which can be obtained by chemical modification of natural NAD(P)/NAD(P)H compounds. Non-limiting examples of artificial NAD(P)/NAD(P)H compounds include 3-acetyl pyridine adenine dinucleotide (3-acetyl NAD) and 3-acetylpyridine adenine dinucleotide phosphate (3-acetyl NADP).

In one embodiment, the coenzyme is a stabilized coenzyme. A stabilized coenzyme within the sense of the present document is a coenzyme that has been chemically modified compared to the native coenzyme, and which compared to the native enzyme has a higher stability at atmospheric pressure towards moisture, temperatures, particularly in the range of 0° C. to 50° C., acids and bases, particularly in the range of pH 4 to pH 10, and/or nucleophiles, such as alcohols and amines for example. Similarly, stabilized coenzymes can be active over a longer period than the native coenzyme under identical environmental conditions.

In one form, the stabilized coenzyme has a higher hydrolytic stability compared to the native coenzyme, and may for example have a complete stability towards hydrolysis under typical test conditions. The stabilized coenzyme may also have a reduced or increased binding constant for the enzyme compared to the native coenzyme. For example, in one aspect the binding constant may be reduced or increased by a factor of two or more.

In forms where an NAD(P)/NAD(P)H compound is used as the coenzyme, it may be selected from compounds of the general formula (I):

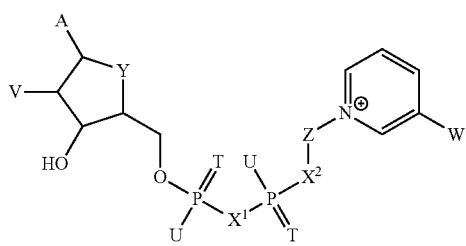

in which
A=adenine or an analogue thereof;
T=in each case independently denotes O or S;
U=in each case independently denotes OH, SH, BH3$^-$ or BCNH$_2^-$;
V=in each case independently denotes OH or a phosphate group, or two groups that form a cyclic phosphate group;
W=COOR, CON(R)$_2$, COR, or CSN(R)$_2$ where R=in each case independently denotes H or a C$_1$-C$_2$ alkyl;
X$^1$, X$^2$=in each case independently denote O, CH$_2$, CHCH$_3$, C(CH$_3$)$_2$, NH, or NCH$^3$;
Y=NH, S, O or CH$_2$;
Z=a linear or cyclic organic residue; or a salt or reduced form thereof.

In one embodiment, the compounds of the general formula (I) contain adenine or adenine analogues such as, for example, C8-substituted and N$_6$-substituted adenine, deaza variants such as 7-deaza, aza variants such as 8-aza or combinations such as 7-deaza or 8-aza or carbocyclic analogues such as formycin where the 7-deaza variants can be substituted at the 7 position by halogen, C$_{1-6}$ alkinyl, C$_{1-6}$ alkenyl or C$_{1-6}$ alkyl.

In a further embodiment, the compounds of the general formula (I) contain adenosine analogues which contain, for example, 2-methoxydeoxyribose, 2'-fluorodeoxyribose, hexitol, altritol or polycyclic analogues such as bicyclo, LNA and tricyclo sugars instead of ribose.

In particular forms of the compounds of the general formula (I), (di) phosphate oxygens can also be replaced isotronically such as, for example, O$^-$ by S$^-$ or BH$_3^-$, O by NH, NCH$_3$ or CH$_2$, and =O by =S. In particular but non-limiting forms, W in the compounds of the general formula (I) is CONH$_2$ or COCH$_3$.

In certain forms of the compounds of the general formula (I), Z is a linear residue containing 4-6 C atoms, and in one particular form 4 C atoms, in which 1 or 2 C atoms are optionally replaced by one or more heteroatoms selected from O, S and N, or a residue comprising a cyclic group containing 5 or 6 C atom s which optionally contains a heteroatom selected from O, S and N as well as optionally one or more substituents, and a residue CR$^4_2$ where CR$^4_2$ is bound to the cyclic group and to X$^2$, where R$^4$ in each case independently denotes H, F, Cl, or CH$_3$.

In one particular form, Z is a saturated or unsaturated carbocyclic or heterocyclic five-membered ring, and more particularly but not exclusively is a compound of the general formula (II)

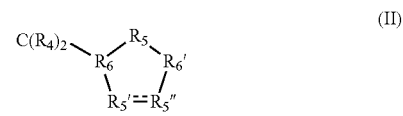

in which a single or double bond can be present between R$_{5'}$ and R$_{5''}$, and in which
R$_4$=H, F, Cl, or CH$_3$;
R5=O or CR$^4_2$;
R$_{5'}$=O, S, NH, NC$_1$-C$_2$-alkyl, CR$^4_2$, CHOH, or CHOCH$_3$, and R$_{5''}$=CR$^4_2$, CHOH, or CHOCH$_3$ if a single bond is present between R$_{5'}$ and R$_{5''}$;
R$_{5'}$=R$_{5''}$=CR$^4_2$ if a double bond is present between R$_{5'}$ and R$_{5''}$;
R$_6$, R6'=each case independently denote CH or CCH$_3$.

In one form, R$_5$ is O or CH$_2$ in the groups of the general formula (II). Furthermore, in one form R$_5$ is selected from CH$_2$, CHOH and NH. In a particular embodiment, R$_{5'}$ and R$_{5''}$ are in each case CHOH. In yet another particular embodiment, R$_{5'}$=NH and R$_{5''}$=CH$_2$. One specific embodiment includes a compound of formula (II) in which R$_4$=H, R$_5$=O or CH$_2$, R$_{5'}$=R$_{5''}$=CHOH and R$_6$=R$_{6'}$=CH.

In yet another particular form, the coenzyme is NAD, NADP, 3-acetyl-NAD or 3-acetyl-NADP. In yet a further variant, a stabilized NAD(P)/NAD(P)H compound or the compound of formula (III) is used as the coenzyme

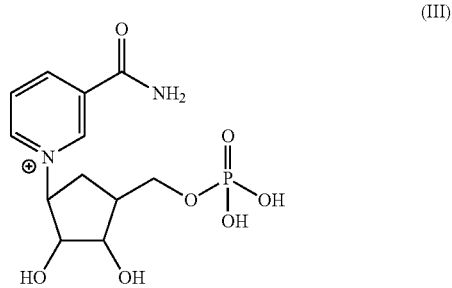 [SMILES: NC(=O)c1ccc[n+](C2CC(COP(=O)(O)O)C(O)C2O)c1]

The stabilized NAD(P)/NAD(P)H compound may in one form include a 3-pyridine carbonyl or a 3-pyridine thiocarbonyl residue which is linked without a glycosidic bond to a phosphorus-containing residue, such as a phosphate residue for example, by a linear or cyclic organic residue. In one particular form, the residue is a cyclic organic residue.

In one non-limiting variant, the stabilized NAD(P)/NAD(P)H compound is selected from compounds of the general formula (I) described above, wherein the group Z and the pyridine residue are not linked together by a glycosidic bond. In this case, the group Z may be a compound of the general formula (II) in which $R_5=CR^4_2$ and the residues $R_4$, $R_{5'}$, $R_{5''}$, $R_6$ and $R_{6'}$ are defined as above. In one particular form, Z is a compound of the formula (II) in which $R_4=H$, $R_5=CH_2$, $R_{5'}=R_{5''}=CHOH$ and $R_6=R_{6'}=CH$.

In still another particular embodiment, the stabilized NAD(P)/NAD(P)H compound is carbaNAD (J. T. Slama, Biochemistry (1988), 27, 183 and Biochemistry (1989), 28, 7688) or carbaNADP. Other stable coenzymes which can be used in the chemical detection reagents described herein are disclosed in Intl Patent Publication Nos. WO 98/33936, WO 01/49247, WO 2007/012494, U.S. Pat. No. 5,801,006, U.S. patent application Ser. No. 11/460,366 and the publication to Blackburn et al. published in *Chemical Communications* (Chem. Comm. (1996), 2765). Each of the above references is hereby incorporated herein by reference in its entirety.

The at least one component that is sensitive to ionizing radiation may also be or include an optical indicator. Any substance that is reducible and undergoes a detectable change in its optical properties when reduced can be used as an optical indicator. Non-limiting examples of such optical properties include color, fluorescence, remission, transmission, polarization and/or refractive index. The determination of the presence and/or the amount of analyte in the sample can be carried out with the naked eye and/or by using an optical or electrochemical method which appears suitable to a person skilled in the art. Examples of optical methods include photometric and fluorimetric methods.

Heteropoly acids such as 2, 18-phosphomolybdic acid for example which are reduced to the corresponding heteropoly blue are preferably used as optical indicators. Furthermore, it is also possible to use quinones such as, for example, resazurin, dichlorophenol indophenol and/or tetrazolium salts as optical indicators. Non-limiting examples of suitable tetrazolium include the products WST-3, WST-4 and WST-5 all commercially available from Dojindo Molecular Technologies, Inc., Kumamoto, Japan.

The form of the diagnostic elements disclosed herein may be any that can be wetted by the sample containing the analyte. Thus, the diagnostic element can contain the component(s) that is/are sensitive to ionizing radiation, such as a polypeptide and/or a coenzyme for example, in one or more reagent layers which optionally contain further reagents that facilitate the qualitative and/or quantitative determination of the analyte. Examples of such further reagents include, amongst others, mediators as well as suitable auxiliary substances and/or additives.

The term "mediator" as used within the scope of this document refers to a chemical compound which reacts with the reduced coenzyme that is obtained by reaction with the analyte, and enables electrons to be transferred to a suitable optical indicator or an optical indicator system or to electrochemical electrodes. Non-limiting examples of mediators include nitrosoanilines, such as [(4-nitrosophenyl)imino] dimethanol hydrochloride for example, quinones, such as phenanthrene quinones, phenanthroline quinones or benzo [h]-quinoline quinones for example, phenazines, such as 1-(3-carboxypropoxy)-5-ethyl-phenazinium trifluoromethane sulfonate for example, and/or diaphorase (EC 1.6.99.2). In one particular form however, the diagnostic elements disclosed herein are mediator-free or contain no mediator which allows side reactions of the mediator to be avoided, and this impairment to the long-term stability of the diagnostic element is therefore eliminated.

In one aspect, the diagnostic elements disclosed herein have, after sterilization and depending on the sterilization method that is used, the at least one component that is sensitive to ionizing radiation in a proportion of ≥80% based on the total amount of the at least one component in the diagnostic element before sterilization in a functional form. In another aspect, the diagnostic elements disclosed herein have, after sterilization and depending on the sterilization method that is used, the at least one component that is sensitive to ionizing radiation in a proportion of ≥90% based on the total amount of the at least one component in the diagnostic element before sterilization in a functional form. Still, in other aspects the diagnostic elements disclosed herein have, after sterilization and depending on the sterilization method that is used, the at least one component that is sensitive to ionizing radiation in a proportion of about 100% based on the total amount of the at least one component in the diagnostic element before sterilization in a functional form.

The term "in a functional form" as used in this document means that the at least one component is present in a chemically active form and can fulfil its intended function in the diagnostic element. In contrast, the term "in a non-functional form" as used in this document means that the at least one component is present in a chemically inactive form or does not fulfil its intended function despite being present in a chemically active form which differs from the form required to exercise the desired function.

In one embodiment, at least 80% of the molecules (including functional and non-functional molecules) of the at least one component that is sensitive to ionizing radiation which were present in the diagnostic element before sterilization are present in an active form after sterilization and can therefore, if necessary together with other components of the chemical detection reagent, affect the desired conversion of the analyte to be determined. The stability of the diagnostic elements disclosed herein towards ionizing radiation is therefore advantageous in that it obviates any need to overdose individual components of the chemical detection reagent (e.g. of an enzyme) relative to other components of the chemical detection reagent which serves to compensate for the sterilization-related loss of functional molecules of the respective component.

In one embodiment, the diagnostic elements disclosed herein include, in addition to the at least one component that is sensitive to ionizing radiation, an element for sample collection (sample collection element), which can be integrated or be present separately. An integrated sample collection element in the sense of this document is understood as a device which is physically connected to the diagnostic element and can transfer the collected sample by suitable means, such as a capillary channel for example, directly onto the diagnostic element.

In contrast, a separate sample collection element is defined herein as a sample collection device that is present separately from the diagnostic element and has no physical connection to the diagnostic element. In this case for example, the sample can be transferred onto the diagnostic element after the sample collection device has been returned to a magazine where the diagnostic element is positioned in the magazine.

It is contemplated that any element may be used as a sample collection element provided that it is able to collect a sample of the analyte and enables the subsequent transfer of the sample onto the diagnostic element. In one non-limiting example, capillary effects are utilized to carry out this transfer. In one particular but non-limiting form, the use of a needle element has proven to be advantageous where the needle element includes a capillary channel to collect the sample and consists of any material. In one aspect, the material is a sterilizable material such as metal or plastic for example.

The diagnostic elements disclosed herein may also be stored together with the sample collection element. In one particular form, one or more diagnostic elements are stored with a needle element in a storage container. It should be understood that the storage container can basically consist of any material and have any form which appear suitable to a person skilled in the art for the purposes of storing diagnostic elements. In one form, the storage containers consist partially or completely of plastic. Non-limiting examples of plastic materials that may be used include those based on polyamide, polycarbonate, polyester, polyethylene and polypropylene.

In one form, the storage container is a magazine which contains several diagnostic elements described herein. The term "several" as used herein means any number >1, but forms in which at least 10 or at least 25 diagnostic elements are stored in the magazine are contemplated and possible. The magazine can have any type of design or configuration, non-limiting examples of which include blister magazines, disk magazines and drum magazines as described for example in EP Patent Application Publication No. 0 951 939 and Int'l Patent Application Publication No. WO 2005/104948. The contents of these references are hereby incorporated herein by reference in their entirety.

The production of the diagnostic elements described herein includes a sterilization process where a diagnostic element that includes a chemical detection reagent containing at least one component that is sensitive to ionizing radiation as well as optionally an integrated or separate sample collection element is provided and then subsequently subjected to a sterilization. In one form, the diagnostic element can be introduced into a suitable storage container, such as a magazine for example, before or after the sterilization. In one particular form, the diagnostic element is introduced into the storage container before carrying out the sterilization.

If the diagnostic element is introduced into a storage container before sterilization, then it is in principle possible to close the storage container before or after sterilizing the diagnostic element. In one form, the container is closed before carrying out the sterilization. In a further form, the production of the diagnostic element includes introducing the diagnostic element into a magazine, closing the magazine and subsequently sterilizing the diagnostic element in the closed magazine. In one aspect of this form, the diagnostic element includes a separate needle element.

The sterilization itself can take place in a variety of ways, non-limiting examples of which include chemical sterilization, sterilization by heating, and sterilization by means of ionizing radiation. In one particular form, the sterilization is ionizing radiation. In one aspect of this form, the ionizing radiation includes electron radiation and/or gamma radiation. In a further aspect, the ionizing radiation is electron radiation.

It should be appreciated that the dose of the ionizing radiation used for sterilization can be selected by a person skilled in the art based on various relevant requirements and factors. In one form, electron radiation used to sterilize the diagnostic element has a dose in the range of 15-35 kGy. In a further form, electron radiation used to sterilize the diagnostic element has a dose in the range of 20-30 kGy. In another form, gamma radiation used to sterilize the diagnostic element has a dose in the range of 15-35 kGy. In yet another form, gamma radiation used to sterilize the diagnostic element has a dose in the range of 20-30 kGy.

After sterilization, the diagnostic element may be packaged in a sterile manner together with the integrated or separate sample collection element as necessary. The sterile packaging enables the diagnostic element to be kept sterile until its later use without requiring a new sterilization. In one form, the diagnostic elements disclosed herein are disposable articles which are not used again after use due to loss of sterility.

The diagnostic elements disclosed herein may include any physical shape familiar to a person skilled in the art which is suitable for determining the presence and/or the amount of an analyte in a sample. Generally speaking, the diagnostic elements each include at least one test area which can be brought into contact with a sample containing the analyte and enables a qualitative and/or quantitative determination of the analyte using suitable means.

In one embodiment, the diagnostic element is designed such that it generates an optically or electrochemically detectable signal in the presence of the analyte to be determined which allows a qualitative and/or quantitative determination of the analyte using optical methods, such as photometry or fluorimetry for example, or electrochemical techniques. Non-limiting examples of designs that the diagnostic elements disclosed herein may have include test elements with an integrated needle element, test tapes, test strips as well as the diagnostic elements described in Int'l Patent Application Publication No. WO 2005/084530 onto which the analyte can be applied in the form of an aqueous or non-aqueous solution for example. The contents of this reference are hereby incorporated herein by reference in their entirety.

The diagnostic elements disclosed herein may be used to determine any biological or chemical substance that can be detected photochemically or electrochemically. In one form, the analyte is selected from the group consisting of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides. In one particular form, the analyte is glucose. It should also be understood that the analyte can be derived from any source. In one aspect however, the analyte is present in a bodily fluid, non-limiting examples of which include whole blood, plasma, serum, lymph fluid, bile, cerebrospinal fluid, extracellular tissue fluid, urine and glandular secretions, such as saliva or sweat for example. In a further aspect, the diagnostic elements described herein are used to determine the presence and/or the amount of an analyte in a sample of whole blood, plasma, serum or extracellular tissue fluid.

The qualitative and/or quantitative determination of the analyte can be carried out in any suitable manner. For example, it is contemplated that all methods for detecting enzymatic reactions known in the art which generate a measurable signal that can be evaluated or read-out manually or using suitable means may be utilized. In one non-limiting form, optical detection methods which include, for example, the measurement of absorption, fluorescence, circular dichroism (CD), optical rotation dispersion (ORD), and/or refractometry are used. In a further form, the analyte may be detected photometrically or fluorometrically indirectly by, for example, means of a fluorometrically detectable change of the coenzyme. Alternatively, the analyte can also be detected electrochemically, where an electrical signal, such as an electrical current, voltage and/or resistance for example, is detected.

Another embodiment concerns a process for producing a diagnostic element and includes the following steps:

(a) providing a diagnostic element including a chemical detection reagent which includes at least one component that is sensitive to ionizing radiation, wherein the at least one component that is sensitive to ionizing radiation is a nicotinamide adenine dinucleotide (NAD/NADH)-dependent or nicotinamide adenine dinucleotide phosphate (NADP/NADPH)-dependent dehydrogenase, and (b) sterilizing the diagnostic element with ionizing radiation.

EXAMPLES

The following examples are for illustration purposes and are not to be construed as limiting the invention disclosed in this document to only the embodiments disclosed in these examples.

In order to evaluate the stability towards ionizing radiation of the chemical system of a diagnostic element that is used to determine glucose and includes glucose dehydrogenase and nicotinamide adenine dinucleotide, the activity of glucose dehydrogenase and the content of nicotinamide adenine dinucleotide in the diagnostic element were determined before and after sterilization with electron radiation or gamma radiation while at the same time varying storage period and storage temperature parameters.

Figure 2:
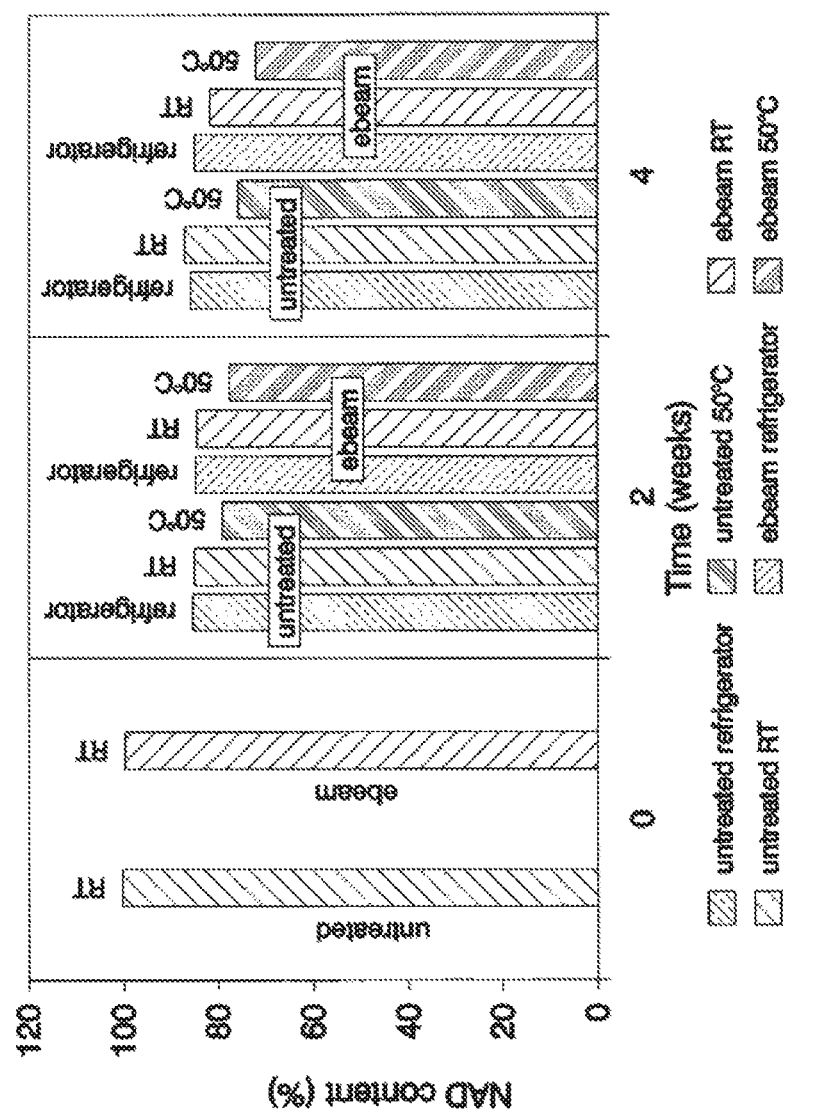
FIG. 2 is a graphical illustration of the content of nicotinamide adenine dinucleotide (NAO) in a diagnostic element that includes glucose dehydrogenase and nicotinamide adenine dinucleotide before and after sterilization with electron radiation (eBeam; dose 25 kGy). The content determination took place immediately after production (0 days) as well as 2 and 4 weeks after storage of the diagnostic element at 5° C. (refrigerator), room temperature (RT) or 50° C.

FIGS. 1 and 2 show a comparison of the activity of glucose dehydrogenase (GlucOH) and a comparison of the content of nicotinamide adenine dinucleotide (NAD) in the diagnostic element described above before and after sterilization with electron radiation. As shown by FIGS. 1 and 2, the activity of GlucDH and the content of NAD is not affected by irradiating the diagnostic element with electron radiation.

Surprisingly, the enzyme activity and the NAD content are each at 100% in a comparison between irradiated and non-irradiated diagnostic elements carried out directly after production of the diagnostic element (0 weeks). As the storage period increases (0 to 4 weeks) and the storage temperature increases (5° C. to 50° C.), the enzyme activity as well as the NAD content decreases in the diagnostic element independently of a possible influence of sterilizing radiation. The prior irradiation of diagnostic elements stored in this manner causes a slight decrease in the GluDH activity and the NAD content which, however, is within the analytical limits of error.

Figure 3:
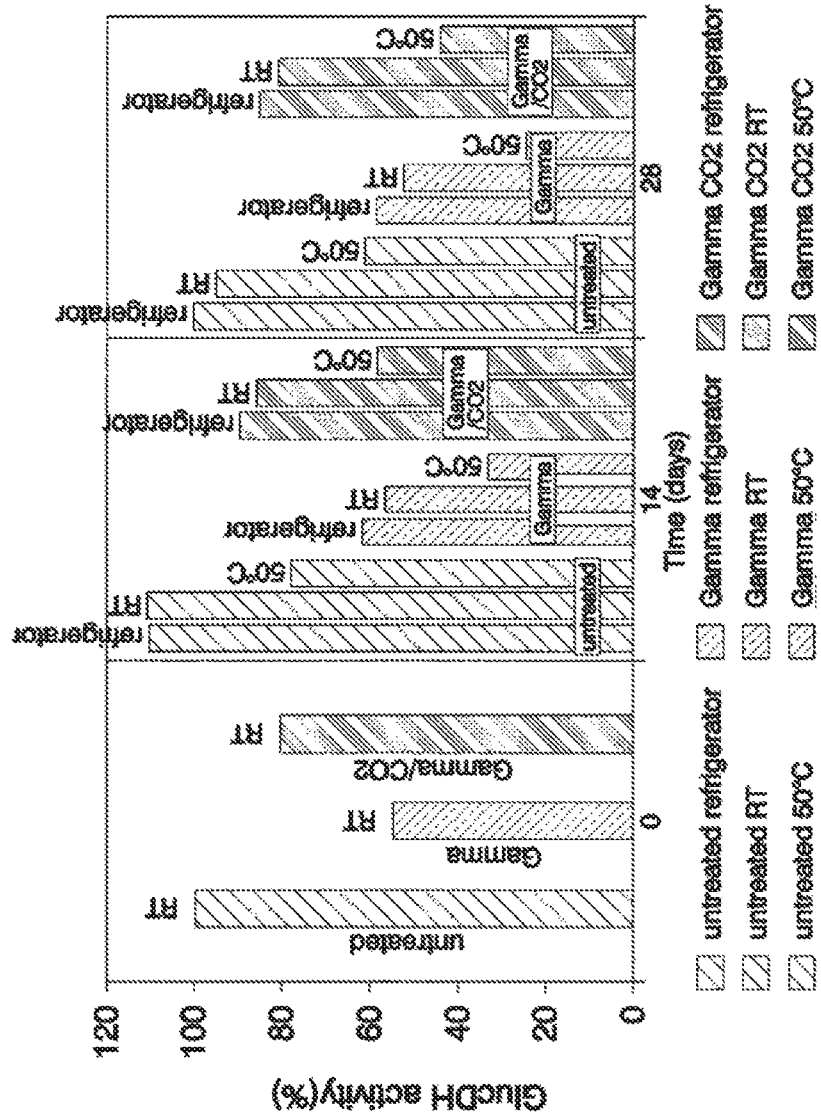
FIG. 3 is a graphical illustration of activity of glucose dehydrogenase (GlucOH) in a diagnostic element that includes glucose dehydrogenase and nicotinamide adenine dinucleotide before and after sterilization with gamma radiation (gamma; dose 25 kGy) or gamma radiation in the presence of carbon dioxide (gamma/$CO_2$; dose 25 kGy). The determination of glucose dehydrogenase activity took place immediately after production (0 days) as well as 2 and 4 weeks after storage of the diagnostic element at 5° C., room temperature (RT) or 50° C.
Figure 4:
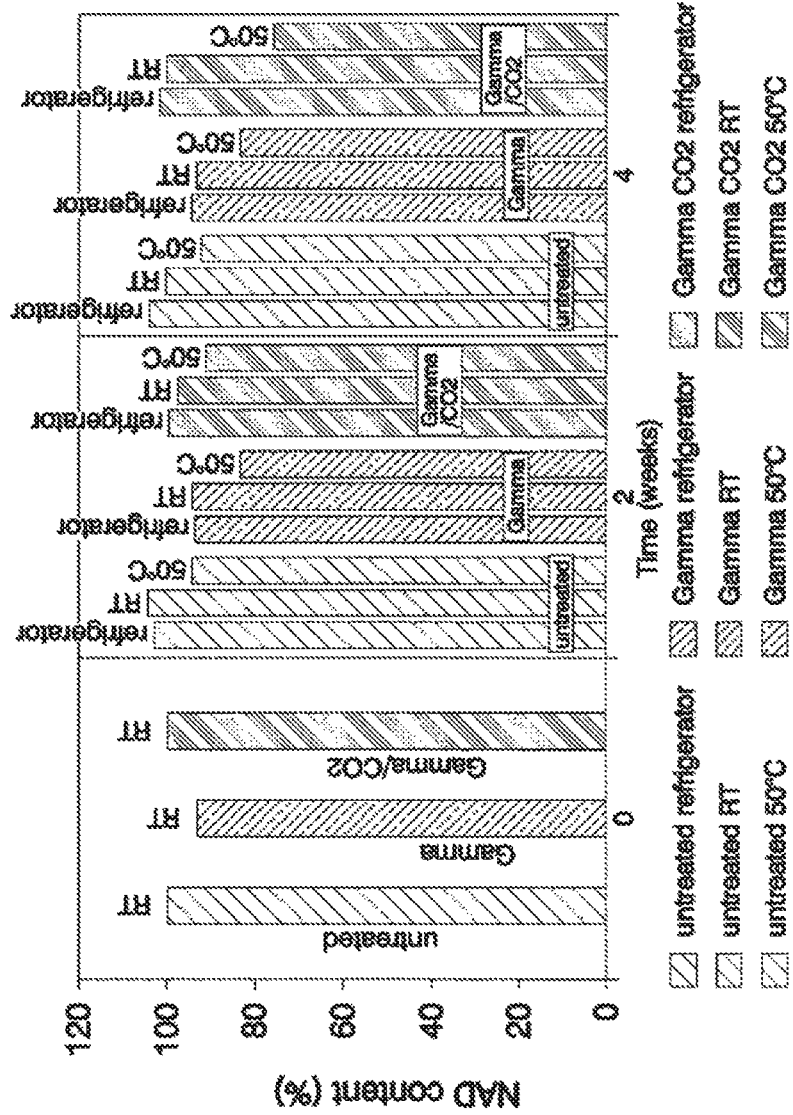
FIG. 4 is a graphical illustration of the content of nicotinamide adenine din ucleotide (NAD) in a diagnostic element that includes glucose dehydrogenase and nicotinamide adenine dinucleotide before and after sterilization with gamma radiation (gamma; dose 25 kGy) or gamma radiation in the presence of carbon dioxide (gamma/$CO_2$; dose 25 kGy). The content determination took place immediately after production (0 days) as well as 2 and 4 weeks after storage of the diagnostic element at 5° C., room temperature (RT) or 50° C.

FIGS. 3 and 4 show a comparison of the activity of glucose dehydrogenase (GlucDH) and a comparison of the content of nicotinamide adenine dinucleotide (NAD) in the diagnostic element described above before and after sterilization with gamma radiation.

In this case it is clear that the enzyme as well as the coenzyme tolerate even high energy gamma radiation albeit to a lesser extent than in the case of sterilization by electron radiation.

Indeed, the enzyme activity in a system sterilized directly after production (0 weeks) decreases to about 55% of the original value, while the damage when using a combination of gamma radiation and carbon dioxide is less at 80% residual enzymatic activity. In the case of the coenzyme, a residual content of NAD of about 90% is detected after sterilization with gamma radiation; when using a combination of gamma radiation and carbon dioxide no difference is found in the NAD content compared to an untreated diagnostic element.

Similar to the experiments carried out with electron radiation, the enzyme activity and the content of coenzyme decrease with increasing storage period (0 to 4 weeks) and increasing storage temperature (5° C. to 50° C.) in an untreated as well as in a diagnostic element treated with gamma radiation or with gamma radiation in combination with carbon dioxide, while the residual enzymatic activity and the content of NAD is only slightly below the values of the corresponding untreated diagnostic elements in the case of the diagnostic elements treated with gamma radiation and carbon dioxide.

Although embodiments of the invention have been described using specific terms, such description is for illustrative purposes only, and it is to be understood that changes and variations obvious to the skilled artisan are to be considered within the scope of the claims that follow and their equivalents.

The invention claimed is:

1. A method of producing a sterilized diagnostic element, the method comprising the steps of:

providing a mediator-free diagnostic test element comprising a chemical detection reagent including at least one component sensitive to ionizing radiation, wherein the at least one component sensitive to ionizing radiation is present in a functional form in a proportion of >80% based on the total amount of the respective component in the diagnostic element before sterilization, and the at least one component sensitive to ionizing radiation includes both an enzyme and a coenzyme, wherein the enzyme is one of a nicotinamide adenine dinucleotide (NAD/NADH)-dependent dehydrogenase or a nicotinamide adenine dinucleotide phosphate (NAD P/NAD PhD-dependent dehydrogenase, and wherein the coenzyme is a NAD(PVNAD (P)H compound; and, sterilizing the mediator-free diagnostic element with ionizing radiation, the ionizing radiation including one or both of electron radiation and gamma radiation.

2. The method of claim 1, wherein the mediator-free diagnostic element further comprises one of an integrated and a separate sample collection element.

3. The method of claim 2, wherein the sample collection element is a needle element.

4. The method of claim 1 further comprising the step of introducing the diagnostic element into a storage container before sterilizing.

5. The method of claim 4, wherein the storage container is a magazine.

6. The method of claim 4 further comprising the step of closing the storage container before sterilizing.

7. The method of claim 1, wherein the ionizing radiation includes electron radiation having a dose in a range of 15-35 kGy.

8. The method of claim 7, wherein the dose is in the range of 20-30 kGy.

9. The method of claim 1, wherein the ionizing radiation includes gamma radiation having a dose in a range of 15-35 kGy.

10. The method of claim 9, wherein the dose is in the range of 20-30 kGy.

11. The method of claim 1, wherein the enzyme is one of a glucose dehydrogenase (EC 1.1.1.47) and a glucose-6-phosphate dehydrogenase (EC 1.1.1.49).

12. The method of claim 1, wherein the NAD(P)/NAD(P)H compound is a stabilized NAD(P)/NAD(P)H compound.

13. The method of claim 12, wherein the stabilized NAD(P)/NAD(P)H compound is a compound according to formula (I), and wherein the compound according to formula (I) is as follows:

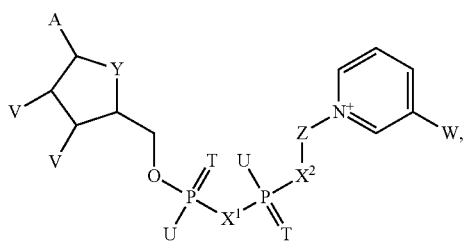

(I)

in which:
A=adenine or an analog thereof,
T=in each case independently denotes O or S,
U=in each case independently denotes OH, SH, $BH_3^-$, or $BCNH_2^-$,
V=in each case independently denotes OH or a phosphate group, or two groups that form a cyclic phosphate group,
W=COOR, $CON(R)_2$, COR, or $CSN(R)_2$ in which R in each case independently denotes H or $C_1$-$C_2$-alkyl,
$X_1$, $X_2$=in each case independently denote O, $CH_2$, $CHCH_3$, $C(CH_3)_2$, NH, or $NCH_3$,
Y=NH, S, O, or $CH_2$,
Z=a linear or cyclic organic residue, or
a salt or a reduced form thereof.

14. The method of claim 13, wherein Z is a saturated or unsaturated carbocyclic or heterocyclic five-membered ring according to formula (II), wherein formula (II) is as follows:

Z=a carbocyclic 5-membered ring of the general formula (II)

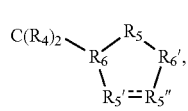

(II)

in which a single bond or double bond is present between R5' and R5", and in which:
R4=in each case independently denotes H, F, Cl, or $CH_3$,
R5=O or $C(R4)_2$,
R5'=O, S, NH, $NC_1$-$C_2$-alkyl, $C(R4)_2$, CHOH, or $CHOCH_3$,
R5"=$C(R4)_2$, CHOH, or $CHOCH_3$ if a single bond is present between R5' and R5",
R5'=R5"=$C(R4)_2$ if a double bond is present between R5' and R5",
R6=in each case independently denotes CH or $CCH_3$, and
R6'=in each case independently denotes CH or $CCH_3$.

15. The method of claim 14, wherein
R4=H,
R5'=CHOH,
R5"=CHOH,
R5=$C(R4)_2$,
R6=CH, and
R6'=CH.

16. The method of claim 12, wherein the stabilized NAD(P)/NAD(P)H compound is a compound according to formula (III), and wherein formula (III) is as follows:

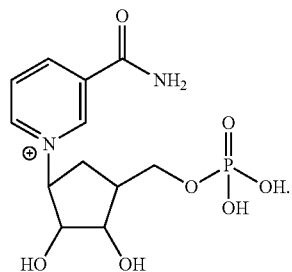

(III)

* * * * *